United States Patent
Chen et al.

(10) Patent No.: US 9,760,979 B2
(45) Date of Patent: Sep. 12, 2017

(54) NAVIGATOR-LESS SEGMENTED DIFFUSION WEIGHTED IMAGING ENABLED BY MULTIPLEXED SENSITIVITY-ENCODED IMAGING WITH INHERENT PHASE CORRECTION

(71) Applicant: Duke University, Durham, NC (US)

(72) Inventors: Nan-kuei Chen, Cary, NC (US); Allen W. Song, Chapel Hill, NC (US)

(73) Assignee: Duke University, Durham, NC (US)

(*) Notice: Subject to any disclaimer, the term of this patent is extended or adjusted under 35 U.S.C. 154(b) by 1113 days.

(21) Appl. No.: 13/928,757

(22) Filed: Jun. 27, 2013

(65) Prior Publication Data

US 2014/0002078 A1  Jan. 2, 2014

Related U.S. Application Data (60) Provisional application No. 61/665,494, filed on Jun. 28, 2012.

(51) Int. Cl.
*G06T 5/00* (2006.01)
*G01R 33/54* (2006.01)
(Continued)

(52) U.S. Cl.
CPC ............ *G06T 5/002* (2013.01); *G01R 33/543* (2013.01); *G01R 33/5615* (2013.01);
(Continued)

(58) Field of Classification Search
CPC .............. G01R 33/543; G01R 33/5611; G01R 33/5616; G01R 33/56341;
(Continued)

(56) References Cited

U.S. PATENT DOCUMENTS

| | | | |
|---|---|---|---|
| 6,842,000 B2* | 1/2005 | Norris | G01R 33/56509 324/309 |
| 7,170,289 B2* | 1/2007 | Kumai | A61B 5/7257 324/307 |

(Continued)

FOREIGN PATENT DOCUMENTS

| | | |
|---|---|---|
| WO | WO 2011/106649 A1 | 9/2011 |
| WO | WO 2012/047771 A2 | 4/2012 |

OTHER PUBLICATIONS

Anderson et al. "Analysis and correction of motion artifacts in diffusion weighted imaging", *Magn. Reson. Med.*, 32: 379-387, 1994.

(Continued)

*Primary Examiner* — Dixomara Vargas
(74) *Attorney, Agent, or Firm* — Myers Bigel, P.A.

(57) ABSTRACT

Diffusion weighted imaging (DWI) and diffusion tensor imaging (DTI) using a new technique, termed multiplexed sensitivity encoding with inherent phase correction, is proposed and implemented to effectively and reliably provide high-resolution segmented DWI and DTI, where shot-to-shot phase variations are inherently corrected, with high quality and SNR yet without relying on reference and navigator echoes. The performance and consistency of the new technique in enabling high-quality DWI and DTI are confirmed experimentally in healthy adult volunteers on 3 Tesla MRI systems. This newly developed technique should be broadly applicable in neuroscience investigations of brain structure and function.

14 Claims, 6 Drawing Sheets
(2 of 6 Drawing Sheet(s) Filed in Color)

Measuring shot-to-shot, motion-induced phase variations of a subject inherently from acquired multiple shot echo planar imaging segments of diffusion weighted image (DWI) data without relying on any navigator signal.

↓

Combining parallel image reconstruction and phase-corrected EPI image reconstruction using the measured phase variations to thereby provide images corrected for motion-induced aliasing artifacts.

(51) Int. Cl.
| | |
|---|---|
| G01R 33/563 | (2006.01) |
| G01R 33/565 | (2006.01) |
| G06T 7/00 | (2017.01) |
| H04N 7/18 | (2006.01) |
| G01R 33/561 | (2006.01) |
| G06T 7/20 | (2017.01) |
| A61B 5/055 | (2006.01) |

(52) U.S. Cl.
CPC . *G01R 33/56341* (2013.01); *G01R 33/56509* (2013.01); *G06T 5/001* (2013.01); *G06T 7/0012* (2013.01); *H04N 7/18* (2013.01); *A61B 5/055* (2013.01); *G01R 33/5611* (2013.01); *G01R 33/5616* (2013.01); *G06T 7/20* (2013.01)

(58) Field of Classification Search
CPC .......... G01R 33/56509; G01R 33/5615; G06T 5/001; G06T 5/002; G06T 7/0012; G06T 7/20; G06T 7/18; H04N 7/18; A61B 5/055
See application file for complete search history.

(56) References Cited

U.S. PATENT DOCUMENTS

| | | | | |
|---|---|---|---|---|
| 7,259,557 | B2* | 8/2007 | Hinks | G01R 33/56554 324/307 |
| 7,375,519 | B2 | 5/2008 | Zur | |
| 7,411,394 | B2* | 8/2008 | Huang | G01R 33/56341 324/307 |
| 7,420,370 | B2* | 9/2008 | Hinks | G01R 33/56554 324/307 |
| 7,696,753 | B2* | 4/2010 | Nozaki | G01R 33/56563 324/307 |
| 2001/0008376 | A1 | 7/2001 | Mock | |
| 2009/0001984 | A1 | 1/2009 | Hwang | |

OTHER PUBLICATIONS

Atkinson et al. "Sampling and Reconstruction Effects Due to Motion in Diffusion-Weighted Interleaved Echo Planar Imaging", *Magn Reson Med*, 44:101-109, 2000.
Butts et al. "Diffusion-Weighted Interleaved Echo-Planar Imaging with a Pair of Orthogonal Navigator Echoes", *MRM* 35:763-770, 1996.
Butts et al. "Interleaved echo planar imaging on a standard MRI system", *Magn Reson Med*, 31(1):67-72, Jan. 1994 (Abstract Only).
Chen et al. "A robust multi-shot scan strategy for high-resolution diffusion weighted MRI enabled by multiplexed sensitivity-encoding (MUSE)", *NeuroImage*, 72, 41-47, 2013.
Chen et al. "Two-Dimensional Phase Cycled Reconstruction for Inherent Correction of Echo-Planar Imaging Nyquist Artifacts", *Magn Reson Med*, 66:1057-1066, 2011.
Griswold et al. "Generalized Autocalibrating Partially Parallel Acquisitions (GRAPPA)", *Magn Reson Med*, 47:1202-1210, 2002.
International Search Report and Written Opinion Corresponding to International Application No. PCT/US2013/048252; Date of Mailing: Sep. 26, 2013; 10 Pages.
Jeong et al. "High-Resolution Human Diffusion Tensor Imaging Using 2-D Navigated Multishot SENSE EPI at 7 T", *Magn Reson Med*, 69:793-802, 2013.
Liu et al. "Self-Navigated Interleaved Spiral (SNAILS): Application to High-Resolution Diffusion Tensor Imaging", *Magn. Reson. Med.*, 52:1388-1396, 2004.
Miller et al. "Nonlinear Phase Correction for Navigated Diffusion Imaging", *Magn Reson Med*, 50:343-353, 2003.
Pipe et al. "Multishot Diffusion-Weighted FSE Using PROPELLER MRI", *Magn Reson Med*, 47:42-52, 2002.
Pruessmann et al. "SENSE: sensitivity encoding for fast MRI", *Magn. Reson. Med.*, Nov. 1999, 42(5):952-962.
Robson et al. "Diffusion-Weighted Multiple Shot Echo Planar Imaging of Humans without Navigation", *MRM*, 38:82-88, 1997.
Sodickson et al. "Simultaneous Acquisition of Spatial Harmonics (SMASH): Fast Imaging with Radiofrequency Coil Arrays", *MRM* 38:591-603, 1977.
Truong et al. "Inherent Correction of Motion-Induced Phase Errors in Multishot Spiral Diffusion-Weighted Imaging", *Magn Reson Med*, 68:1255-1261, 2012.
Andersson et al. "A model-based method for retrospective correction of geometric distortions in diffusion-weighted epi", Neuroimage, 16 (1), 177-99, May 2002.
Atkinson et al. "Nonlinear phase correction of navigated multi-coil diffusion images", Magn Reson Med. 56 (50, 1135-9, Nov. 2006.
Bammer et al. "Augmented generalized SENSE reconstruction to correct for rigid body motion", Magn Reson Med, 57 (1), 90-102, Jan. 2007.
Bammer et al. "Diffusion-weighted imaging with navigated interleaved echo-planar imaging and a conventional gradient system", Radiology, 211 (3), 799-806, Jun. 1999.
Butts et al. "Interleaved echo planar imaging on a standard MRI system", *Magn Reson Med*, 31(1):67-72, Jan. 1994.
Bydder et al. "SMASH navigators", Magn Reson Med, 49 (3), 493-500, Mar. 2003.
Farzaneh et al. "Analysis of t2 limitations and off-resonance effects on spatial resolution and artifacts in echo-planar imaging", Magn Reson Med. 14 (1), 123-39, Apr. 1990.
Feinberg et al. "Multiplexed echo planar imaging for sub-second whole brain FMRI and fast diffusion imaging", PLoS One, 5 (12), e15710, 2010.
Holdsworth et al. "Diffusion tensor imaging (dti) with retrospective motion correction for large-scale pediatric imaging", J. Magn Reson Imaging, 36 (4), 961-71, Oct. 2012.
Jezzard et al. "Characterization of and correction for eddy current artifacts in echo planar diffusion imaging", Magn Reson Med. 39, (5), 801-812, May 1998.
Le Bihan et al. "Separation of diffusion and perfusion in intravoxel incoherent motion MR imaging", Radiology, 168 (2), 497-505, 1998.
Li et al. "X-PROP: a fast and robust diffusion-weighted propeller technique", Magn Reson Med 66 (2), 341-7, Aug. 2011.
Mohammadi et al. "Correcting eddy current and motion effects by affine whole-brain registrations: evaluation of three-dimensional distortions and comparison with slicewise correction", Magn Reson Med, 64 (4), 1047-56, Oct. 2010.
Moseley et al. "Diffusion-weighted MR imaging of anisotropic water diffusion in cat central nervous system", Radiology, 176 (2), 439-45, Aug. 1990.
Porter et al. "High resolution diffusion-weighted imaging using readout-segmented echo-planar imaging, parallel imaging and a two-dimensional navigator-based reacquisition", Magn Reson Med., 62 (2), 468-75, Aug. 2009.
Rudin et al. Nonlinear total variation based noise removal algorithms, Physica D, 6 (1-4), 259-268, 1992.
Skare et al. "Propeller EPI in the other direction", Magn Reson Med. 55 (6), 1298-307, Jun. 2006.
Turner et al. "Echo-planar imaging of duffusion and perfusion", Magn Reson Med. 19 (2), 247-53, Jun. 1991.
Wang et al. "PROPELLER EPI: an MRI technique suitable for diffusion tensor imaging at high field strength with reduced geometric distortions", Magn Reson Med. 54 (5), 1232-40, Nov. 2005.
International Preliminary Report on Patentability. Corresponding to International Application No. PCT/US2013/048252; Date of Mailing: Jan. 8, 2015; 7 Pages.
Extended European Search Report for related European Application No. EP13809232.5, date May 30, 2016, 11 pages.
Mani et al., Accelerating Non-Cartesian Sense for Large Coil Arrays: Application to Motion Compensation in Multishot DWI, 2012 IEEE International Symposium on Biomedical Imaging (ISBI), pp. 406-409.

(56) References Cited

OTHER PUBLICATIONS

Uecker et al., Inverse Reconstruction Method for Segmented Multishot Diffusion-Weighted MRI with Multiple Coils, Magnetic Resonance in Medicine, 2000, pp. 1342-1348, vol. 62.
Basser et al., "MR Diffusion Tensor Spectroscopy and Imaging," Biophysical Journal, vol. 65, Jan. 1994, pp. 259-267.
Liu et al., "Self-Navigated Interleaved Spiral (SNAILS): Application to High-Resolution Diffusion Tensor Imaging," Magnetic Resonance in Medicine, vol. 52, 2004, pp. 1388-1396.
Pruessmann et al, "Sense: Sensitivity Encoding for Fast MRI," Magnetic Resonance in Medicine, vol. 42, 1999, pp. 952-962.

* cited by examiner

Measuring shot-to-shot, motion-induced phase variations of a subject inherently from acquired multiple shot echo planar imaging segments of diffusion weighted image (DWI) data without relying on any navigator signal.

↓

Combining parallel image reconstruction and phase-corrected EPI image reconstruction using the measured phase variations to thereby provide images corrected for motion-induced aliasing artifacts.

FIG. 4

NAVIGATOR-LESS SEGMENTED DIFFUSION WEIGHTED IMAGING ENABLED BY MULTIPLEXED SENSITIVITY-ENCODED IMAGING WITH INHERENT PHASE CORRECTION

RELATED APPLICATIONS

This application claims the benefit of and priority to U.S. Provisional Application Ser. No. 61/665,494, filed Jun. 28, 2012, the contents of which are hereby incorporated by reference as if recited in full herein.

STATEMENT OF FEDERAL SUPPORT

This invention was made with government support under Grant Nos. R01 NS 074045, R01 EB 009483, and R01 NS 075017 awarded by the National Institutes of Health. The United States government has certain rights in this invention.

BACKGROUND

Diffusion-weighted imaging (DWI) techniques, including diffusion tensor imaging (DTI), are now among the most powerful MR imaging tools for assessing the neuronal microstructures in vivo [1, 2, 3]. To date, DWI data are commonly acquired with single-shot pulse sequences, such as single-shot echo-planar imaging (EPI) [4] and single-shot spiral imaging, to avoid significant artifacts resulting from amplified motion-induced phase errors in segmented DWI [5]. However, the image quality can be low and the spatial resolution limited in single-shot DWI [6]. The significant geometric distortions and limited spatial resolution make it difficult to measure diffusion properties at high spatial fidelity [7].

Recent efforts have been made to address the limitations of single-shot DWI. First, using parallel imaging techniques (e.g., SMASH [8], SENSE [9] and GRAPPA [10] among others), EPI and spiral imaging based DWI with reduced geometric distortion can be reconstructed from undersampled k-space data at a chosen acceleration factor. A major concern with the conventional parallel MRI procedures is that the noises may be undesirably amplified, especially when a high acceleration factor is used. Second, segmented EPI, spiral imaging and fast spin-echo pulse sequences with embedded navigator echoes have been developed to produce DWI data that are less distorted and insensitive to motion-induced phase variations between shots, with shortened readout window and phase correction based on navigator signals [11, 12, 13, 14, 15, 16]. It has also been shown that the linear terms of motion-induced phase errors may even be estimated from segmented DWI with an iterative computation algorithm in post-processing without exclusively relying on navigator echoes [17, 18]. A clear advantage of the navigator-based segmented DWI, as compared with parallel DWI that is susceptible to undesirable noise amplification, is the high SNR. However, a potential concern for this technique is that the shot-to-shot phase variations due to local and nonlinear motion (e.g., in the brainstem [19]) can only be accurately measured with high-resolution navigator echoes, at the significant cost of imaging throughput.

SUMMARY OF EMBODIMENTS OF THE INVENTION

To simultaneously address the above-mentioned technical challenges, a new technique is described that uses a multiplexed sensitivity-encoding with inherent phase correction to achieve high spatial resolution, high SNR, low geometric distortions, and minimal motion-induced phase errors—all inherently without the need for navigator or reference echoes. Specifically, as compared with the conventional parallel DWI, the noise amplification resulting from parallel reconstruction can be greatly reduced with the techniques described herein. As compared with the conventional segmented DWI, shot-to-shot motion-induced phase variations can be accurately measured and corrected, at high spatial resolution, inherently from the acquired segmented DWI data without relying on any navigator signal.

Diffusion weighted imaging (DWI) and diffusion tensor imaging (DTI) data are conventionally acquired with single-shot echo-planar imaging (EPI) or spiral imaging, to avoid potential artifacts resulting from shot-to-shot motion-induced phase variations in multi-shot acquisitions. However, the image quality and resolution are less than optimal in single-shot scans. It has been shown that it is feasible to produce high-quality and high-resolution navigator-based segmented DWI and DTI data, after the shot-to-shot phase variations are corrected using the information derived from the embedded navigator echoes. However, the phase variations due to local and nonlinear motion may not always be accurately measured with low-resolution navigator echoes. To address these challenges, a new procedure, termed multiplexed sensitivity-encoded imaging with inherent phase correction, is described to allow navigator-less segmented DWI and DTI with high quality and high signal-to-noise ratio (SNR), in which shot-to-shot phase variations are inherently estimated at high spatial-resolution and then used to produce aliasing-free DWI and DTI data.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1: (a,b): Four-shot segmented DWI (corresponding to two b-directions from a 15-direction DTI scan) are susceptible to aliasing artifacts. (c,d): The aliasing artifact can be reduced in images reconstructed by combining magnitude signals of four SENSE-produced images (from four EPI segments), although the noises are undesirably amplified. (e): The motion-induced phase variations in the second, third, and fourth EPI segments, using first EPI segment as a zero-phase reference, for data shown in (a). (f): The motion-induced phase variations for data shown in (b). (g, h): The spatially-smoothed phase variation maps. (i): An image reconstructed with Equation 1 from one of the eight-channel coil of data shown in (a). (j): An image reconstructed with Equation 1 from one of the eight-channel coil of data shown in (b). (k,l): High-quality and high-SNR DWI reconstructed with Equation 3. (m): The voxels within the square ROI of image (c). (n): The voxels within the square ROI of image (k).

FIG. 2: (a): Four-shot segmented DTI data of 15-direction are susceptible to motion-induced phase errors. (b): Using the new technique, the motion-induced aliasing artifacts can be eliminated. (c): The FA map generated from the conventional SENSE reconstruction has a low SNR. (d): The SNR is significantly improved in FA map produced with the new technique.

FIG. 3: (a): Pronounced motion-induced artifacts appear in segmented DWI images when there exist local and nonlinear motions (e.g., in the brainstem). (b): The aliasing artifact can be eliminated with the new technique. (c): The SNR is low in the FA map produced with the conventional SENSE procedure. (d): Using the new technique, the FA map of high-SNR can be achieved.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

A. Theory and Methods

Figure 1A:
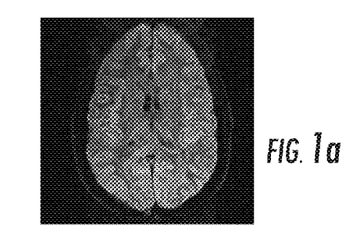
Figure 1B:
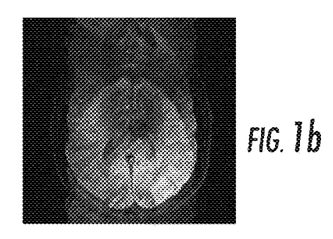
Figure 1C:
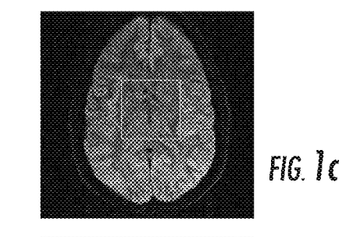
Figure 1D:
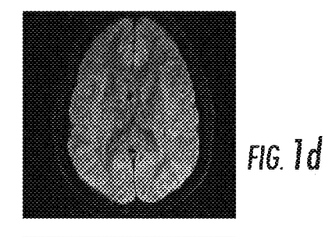

DWI data obtained with segmented EPI pulse sequence are highly susceptible to aliasing artifacts resulting from shot-to-shot motion-induced phase variations. Here, without the loss for generality for multi-shot acquisitions, all DWI data was acquired using a 4-shot segmented EPI acquisition. For example, FIGS. 1a and 1b illustrate two DWI images (corresponding to two b-directions from a 15-direction DTI scan), obtained with a 4-shot segmented diffusion-weighted EPI using an 8-channel receiver coil. It is demonstrated that the levels of aliasing artifacts due to motion-induced phase variations among shots may be inconsistent, depending on the degree of intrascan motion. An effective way to remove these shot-to-shot motion-induced aliasing artifacts is to use parallel imaging procedures to reconstruct aliasing-free images from each of the 4 segments. For example, FIGS. 1c and 1d show the summation of 4 SENSE-based parallel images (from 4 different segments) [9], for the two DWI datasets. It can be seen that, although the motion-induced aliasing artifact can be minimized with parallel imaging reconstruction, the noises are amplified and noticeably higher than those in images shown in FIGS. 1a and 1b (e.g., for voxels inside the square of FIG. 1c).

Figure 1E:
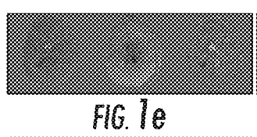
Figure 1F:
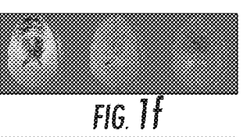

In the absence of large scale intra-scan motion, DWI images reconstructed from four EPI segments are expected to have similar magnitude signals but very different phase signals, reflecting the amplified motion-induced phase variations in the presence of diffusion weighting gradients. For example, FIG. 1e shows the relative phase changes in images reconstructed with the conventional SENSE method from the second, third and fourth EPI segments, in reference to the first EPI segment, for the data set shown in FIG. 1a. Similarly, FIG. 1f shows the relative phase changes in images reconstructed from the second, third and fourth EPI segments, using the first EPI segment as a zero-phase reference, for the data set shown in FIG. 1b. Note that the aliasing artifact in the image shown in FIG. 1b is significantly higher than that in the image shown in FIG. 1a, because there exists more significant inter-segment phase variation as illustrated in FIG. 1f (particularly the second EPI segment shown in the left-most image of FIG. 1f).

The information on phase inconsistency information, shown in FIGS. 1e and 1f, can actually be used to reconstruct N-shot segmented EPI images with reduced aliasing artifact by solving Equation 1 or Equation 2 in its matrix form, without relying on coil sensitivity profiles or parallel imaging procedures.

$$u = Ep \quad (1)$$

$$\begin{bmatrix} u_1 \\ u_2 \\ \vdots \\ u_N \end{bmatrix} = \frac{1}{N} \begin{bmatrix} e^{i\frac{2\pi}{N} \cdot 0 \cdot 0} & e^{i\frac{2\pi}{N} \cdot 0 \cdot 1} & \cdots & e^{i\frac{2\pi}{N} \cdot 0 \cdot (N-1)} \\ e^{i\frac{2\pi}{N} \cdot 1 \cdot 0} e^{i\Theta|_1^2} & e^{i\frac{2\pi}{N} \cdot 1 \cdot 1} e^{i\Theta|_2^2} & \cdots & e^{i\frac{2\pi}{N} \cdot 1 \cdot (N-1)} e^{i\Theta|_N^2} \\ \vdots & \vdots & \ddots & \vdots \\ e^{i\frac{2\pi}{N} \cdot (N-1) \cdot 0} e^{i\Theta|_1^N} & e^{i\frac{2\pi}{N} \cdot (N-1) \cdot 1} e^{i\Theta|_2^N} & \cdots & e^{i\frac{2\pi}{N} \cdot (N-1) \cdot (N-1)} e^{i\Theta|_N^N} \end{bmatrix} \begin{bmatrix} p_1 \\ p_2 \\ \vdots \\ p_N \end{bmatrix} \quad (2)$$

where p in Equation 1 is a N×1 column vector with its elements $p_n$ representing unaliased image signals at location n (n=1 . . . N; separated by $$\frac{FOV_y}{N}$$

along the phase-encoding direction); u in Equation 1 is a N×1 column vector with its elements $u_k$ representing aliased image signals of the k-th EPI segment; E in Equation 1 is a N×N matrix, with $\Theta|_n^k$ in Equation 2 representing the motion-induced phase errors at location n for the k-th EPI segment, using data from the first EPI segment as the zero-phase reference.

Figure 1G:
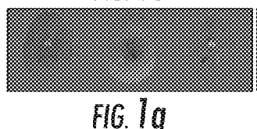
Figure 1H:
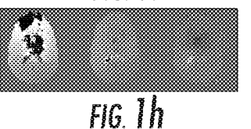
Figure 1I:
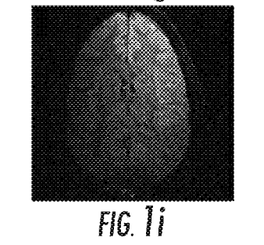
Figure 1J:
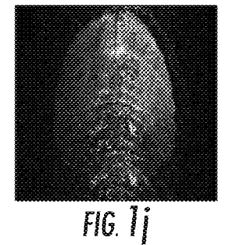
Figure 1K:
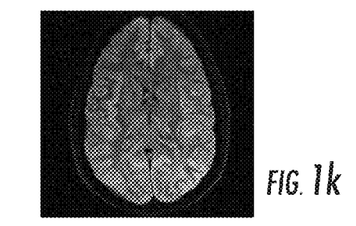
Figure 1L:
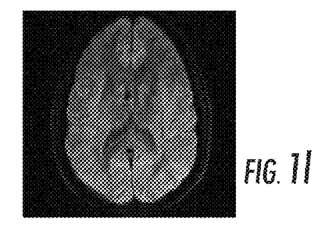
Figure 1M:
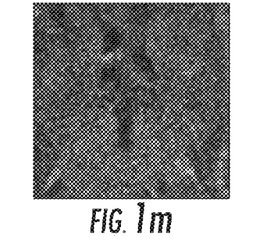
Figure 1N:
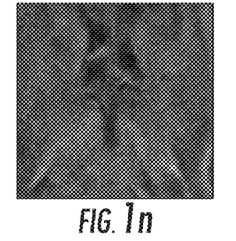

The SENSE-based phase profiles (FIGS. 1e and 1f) can first be unwrapped and spatially smoothed with the total variation algorithm [20], which preserves the sharp edges (e.g., near the boundary of white matter and ventricles) as shown in FIGS. 1g and 1h. They can be subsequently used to produce segmented EPI data with reduced aliasing artifact based on Equation 1 or 2. The reconstructed images (at two representative diffusion directions) for 1 of the 8 coils are shown in FIGS. 1i and 1j, for the datasets corresponding to FIGS. 1a and 1b, respectively. Even though the aliasing artifacts can be reduced with this approach, the residual artifact could still be pronounced when the matrix inversion (with 4 equations and 4 unknowns for 4-shot EPI) is ill-conditioned (e.g., FIG. 1j). It should be noted that the segmented EPI reconstruction based on Equations 1 and 2 uses a relationship that is independent of the sensitivity encoding and thus can be applied to single-coil data (e.g., FIGS. 1i and 1j), although the phase information is initially estimated from images produced by the SENSE procedure.

To this end, the parallel image reconstruction (that produces FIGS. 1c and 1d) and the phase-corrected segmented EPI reconstruction (that produces FIGS. 1i and 1j) can be combined to significantly improve the conditioning number of the matrix inversion, rightly assuming that magnitude signals remain unchanged across multiple EPI segments, as shown in Equation 3.

$$\begin{bmatrix} u|_1^w \\ u|_2^w \\ \vdots \\ u|_N^w \end{bmatrix} = \frac{1}{N} \begin{bmatrix} S\big|_1^w e^{i\frac{2\pi}{N}\cdot 0\cdot 0} & S\big|_2^w e^{i\frac{2\pi}{N}\cdot 0\cdot 1} & \cdots & S\big|_N^w e^{i\frac{2\pi}{N}\cdot 0\cdot (N-1)} \\ S\big|_1^w e^{i\frac{2\pi}{N}\cdot 1\cdot 0} e^{i\Theta|_1^2} & S\big|_2^w e^{i\frac{2\pi}{N}\cdot 1\cdot 1} e^{i\Theta|_2^2} & \cdots & S\big|_N^w e^{i\frac{2\pi}{N}\cdot 1\cdot (N-1)} e^{i\Theta|_N^2} \\ \vdots & \vdots & \ddots & \vdots \\ S\big|_1^w e^{i\frac{2\pi}{N}\cdot (N-1)\cdot 0} e^{i\Theta|_1^N} & S\big|_2^w e^{i\frac{2\pi}{N}\cdot (N-1)\cdot 1} e^{i\Theta|_2^N} & \cdots & S\big|_N^w e^{i\frac{2\pi}{N}\cdot (N-1)\cdot (N-1)} e^{i\Theta|_N^N} \end{bmatrix} \begin{bmatrix} p_1 \\ p_2 \\ \vdots \\ p_N \end{bmatrix} \quad (3)$$

where $s|_n^w$ represents the known coil sensitivity profile for coil number w (w=1,2, . . . W; with W is the total coil number) at location n; $\Theta|_n^k$ represents the motion-induced phase errors at location n for the k-th EPI segment, using data from the first EPI segment as the zero-phase reference; $u|_k^w$ represents aliased image signals of the k-th EPI segment measured with coil number w.

DWI data with significantly improved image quality can be produced with Equation 3 (that solves 4 unknowns with 32 equations for 4-shot EPI data shown in FIG. 1), and this procedure can be termed "multiplexed sensitivity-encoding with inherent phase correction". The images reconstructed with the new procedure, from DWI data corresponding to FIGS. 1a and 1b, are shown in FIGS. 1k and 1l respectively. It can be seen that 1) the motion-induced artifacts are effectively eliminated as compared with the conventional segmented EPI reconstruction, and 2) the SNR is significantly higher than that in images produced with the conventional SENSE procedure (e.g., FIGS. 1c and 1d). The voxels in the chosen square (FIG. 1e) in FIGS. 1c and 1k are displayed separately in FIGS. 1m and 1n, respectively, illustrating the SNR improvement associated with the new procedure.

To evaluate the performance and confirm the reliability of the new technique, DWI and DTI data were obtained from 5 healthy volunteers on 3 Tesla MRI systems (GEHC HD and MR750, Waukesha, Wis.) equipped with an 8-channel receiver coil. T2-weighted images and either DTI (of 15 b-directions) or DWI data, with b=500 sec/mm², were acquired using a 4-shot segmented EPI pulse sequence with a twice-refocused spin-echo scheme to minimize the eddy current induced geometric distortions [21]. The acquired data were processed with the following steps. First, the recently developed phase-cycled reconstruction procedure [22] was used to measure the 2D phase errors resulting from odd-even echo inconsistencies in T2-weighted data, and the information was used to suppress the Nyquist artifacts in both T2-weighted and diffusion-weighted images. Second, the coil sensitivity profiles were estimated from segmented EPI based T2-weighted images. Third, using the conventional SENSE reconstruction procedure, four full-FOV images were reconstructed from four DWI segments, and the motion-induced phase variations in the second, third and fourth segments were calculated using the first DWI segment as a zero-phase reference (e.g., FIGS. 1e and 1f). Fourth, the phase maps derived from step 3 were spatially smoothed with the total variation algorithm (e.g., FIGS. 1g and 1h). Fifth, the smoothed phase maps (step 4) and the coil sensitivity profiles (step 2) were used to reconstruct aliasing-free DWI or DTI images from the Nyquist-corrected DWI or DTI data, based on Equation 3. Sixth, the eigenvectors and the fractional anisotropy (FA) values were calculated from the aliasing-free DTI data. Seventh, in order to illustrate the SNR improvement uniquely provided by the new procedure, another set of aliasing-free DWI and DTI data were generated by summing the magnitude maps derived from four EPI segments with the conventional SENSE procedure (i.e., in step 3 described above), and the quality of the resultant FA maps were then assessed.

B. Results

Figure 2A:
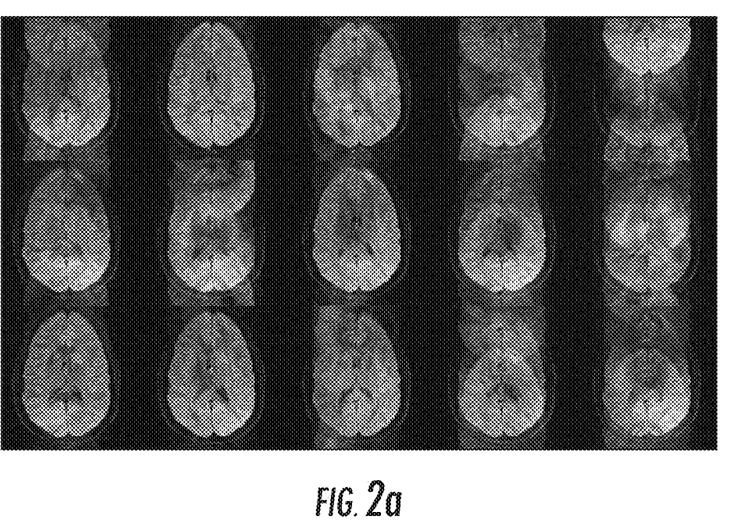
Figure 2B:
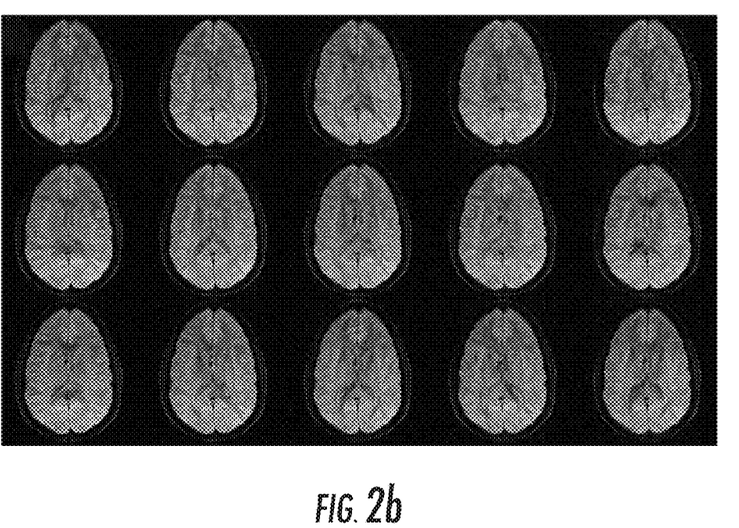
Figure 2C:
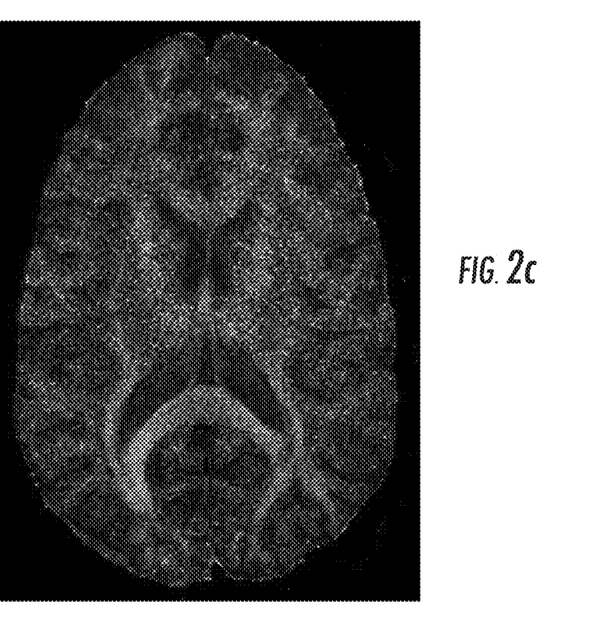
Figure 2D:
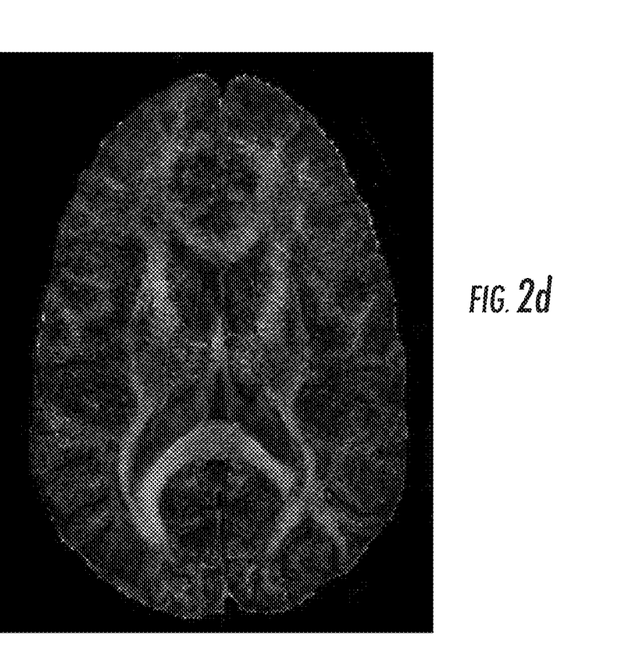

Using the new procedure, high-SNR and artifact-free images can be reliably acquired using segmented DWI, as confirmed from all 5 healthy volunteers. FIG. 2a shows the Nyquist-corrected DWI images produced by the conventional segmented EPI reconstruction (i.e., a direct k-space data combination), corresponding to 15 b-directions obtained from one representative participant. As expected, the levels of motion-induced aliasing artifacts vary significantly, depending on the degree of intrascan motion. FIG. 2b shows that the motion induced aliasing artifacts can be effectively eliminated using multiplexed sensitivity-encoding with inherent phase correction, regardless of the levels of aliasing artifacts in the raw DWI data. It should be noted that, even though the motion-induced aliasing artifacts can also be effectively suppressed with a conventional SENSE procedure (i.e., step 7 described in the last paragraph of the Theory and Methods section), the resultant images have significantly lower SNRs (e.g., FIGS. 1c and 1d). FIGS. 2c and 2d compare the FA maps produced with the conventional SENSE procedure for individual segments (i.e., combination of 4 SENSE produced images) and the new multiplexed sensitivity-encoding with inherent phase correction technique, respectively. It is demonstrated that multiplexed sensitivity-encoding with inherent phase correction DWI has a significantly higher SNR.

Figure 3A:
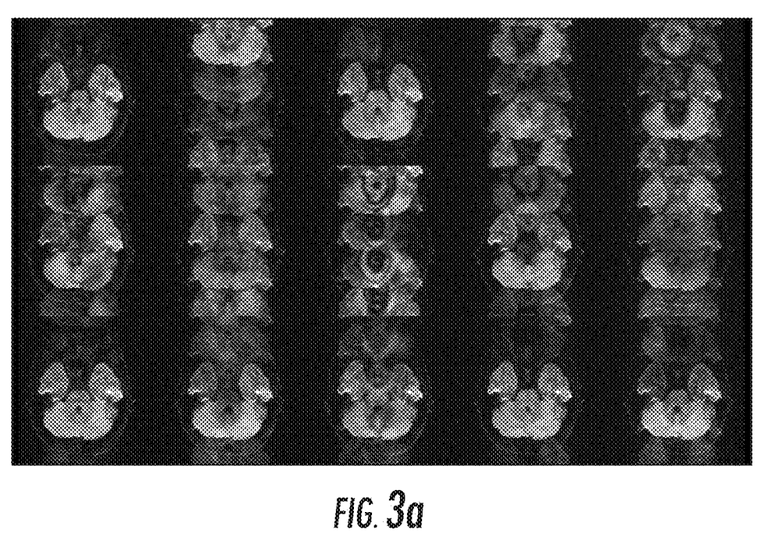
Figure 3B:
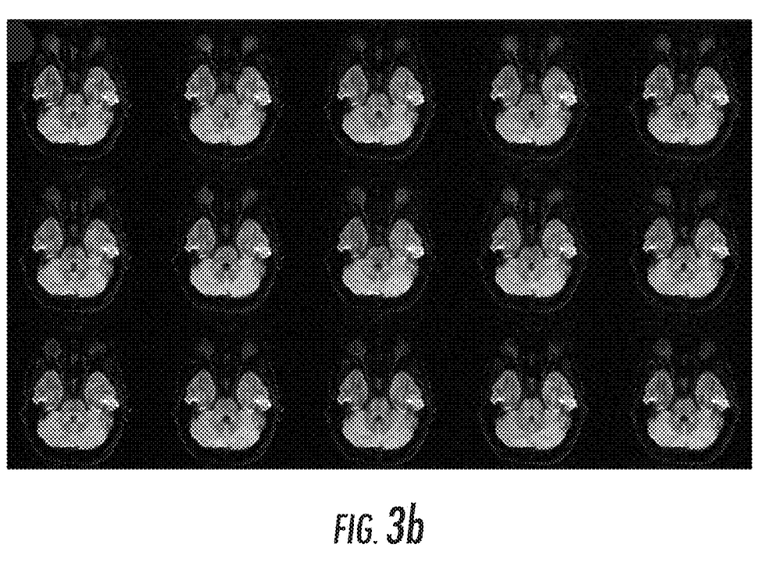
Figure 3C:
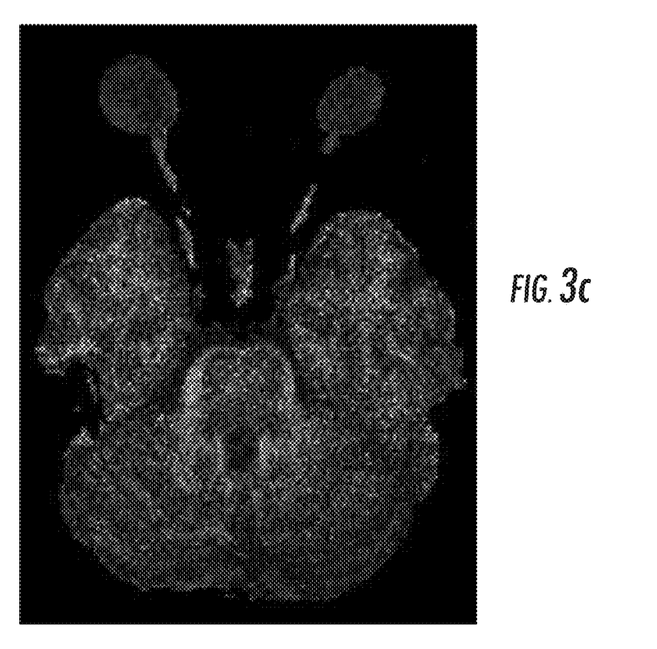
Figure 3D:
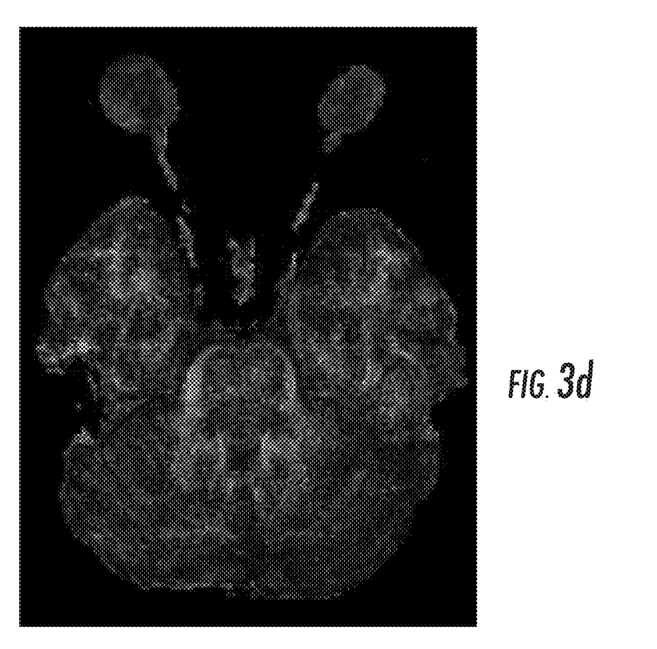
Figure 4:
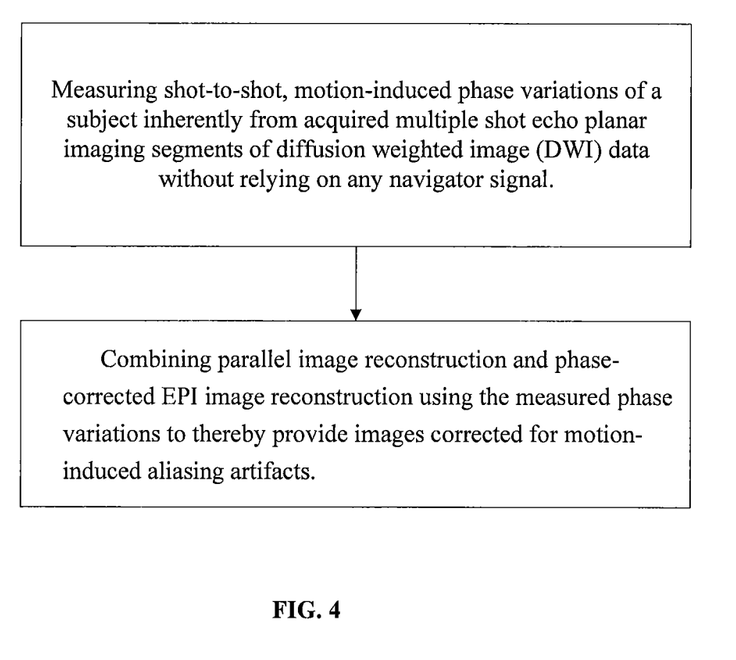
FIG. 4 is a block diagram that illustrates the method steps of original claim 2.

FIGS. 3a and 3b show the DWI data before and after applying the multiplexed sensitivity-encoding with inherent phase correction procedure, respectively, for another slice that includes the brainstem and eyes where local motion artifacts are prevalent. It can be seen that, because of the local motion, the aliasing artifacts can be highly significant in most of the segmented DWI images (FIG. 3a). Furthermore, the aliased signals of the eyes may destructively interfere with the brain images. These pronounced aliasing artifacts can all be effectively eliminated by the new procedure, as demonstrated in FIG. 3b. Again, even though the motion-induced aliasing artifact can also be minimized with the conventional SENSE reconstruction in individual segments, the resultant DWI data and FA map have lower SNR (FIG. 3c) as compared with the multiplexed sensitivity-encoding with inherent phase correction produced results (FIG. 3d).

C. Discussion

In comparison with the conventional navigator-based segmented DWI, the new multiplexed sensitivity-encoding with inherent phase correction technique, which requires neither navigator nor reference echoes, has a few advantages. First, the imaging throughput of navigator-less segmented DWI is potentially higher than that of navigator-based segmented DWI. Second, the local and nonlinear motion-induced phase variations (e.g., in brainstem) can be inherently measured at high spatial resolution with the multiplexed sensitivity-encoding with inherent phase correction method. On the other hand, when using the conventional navigator-based segmented DWI, the nonlinear phase variations can only be measured with a high-resolution navigator echo, at the cost of significant reduction in imaging throughput.

A limitation of the multiplexed sensitivity-encoding with inherent phase correction method is that the number of EPI segments cannot be higher than the number of coils; otherwise the phase variation maps (e.g., shown in FIGS. 1e and 1f) cannot be reliably estimated with the conventional SENSE procedure (i.e., step 3 described in the last paragraph of the Theory and Methods section). It should be noted that, in contrast to the conventional SENSE based DWI, the new procedure has a significantly improved matrix inversion conditioning (i.e., Equation 3) even when the number of EPI segments is not significantly smaller than the number of coils. For example, as demonstrated by FIGS. 1 to 3, high-quality DWI and DTI maps can be obtained from a 4-shot segmented EPI acquisition using an 8-channel receiver coil.

It should also be noted that, in this report, the issues related to shot-to-shot motion induced phase inconsistencies in segmented EPI are addressed, while assuming that there is no large-scale intrascan motion and the magnitude signals remain constant across multiple EPI segments, as indicated by Equation 3. This condition is mostly met for cooperative subjects. On the other hand, in the presence of very large scale motion when intrascan motion can be significant, it would be inappropriate to assume that the magnitude signals remain constant across multiple EPI segments. In this case, the new algorithm may need to be further modified or expanded to accommodate for large-scale intrascan motion.

As compared with single-shot EPI based DWI, the spatial-resolution and spatial accuracy can be significantly improved with the segmented EPI based DWI. The high-resolution DWI capability enabled by the multiplexed sensitivity-encoding with inherent phase correction algorithm/method should prove highly valuable for assessing microstructures in anatomic regions of interest that are small in size, such as cortical gray matter layers, gray-white matter boundaries, and the sub-divisions of the basal ganglia and thalamus [23]. In addition, the segmented EPI pulse sequence makes it possible to acquire DWI data at a short TE, which in turn result in increases of the SNR as compared with the single-shot EPI data of the same voxel size.

Even though the multiplexed sensitivity-encoding with inherent phase correction procedure is only demonstrated with segmented DWI in this study, the technique can also be applied to eliminate motion-induced artifacts in segmented high-resolution DWI and DTI with non-Cartesian k-space trajectories (such as spiral imaging) [18]. It is expected that multiplexed sensitivity-encoding with inherent phase correction may also be applied to improve the quality for other types of studies where high spatial resolution is desired, such as those in functional MRI (fMRI) in the presence of phase variations over time due to physiological motions or magnetic field drifting.

In conclusion, embodiments of the invention can provide a new and highly practical technique to allow high-resolution DWI with high spatial fidelity and SNR, yet without the need for navigator and reference echoes. In contrast to the conventional parallel DWI, the multiplexed sensitivity-encoding with inherent phase correction based DWI reconstruction is not susceptible to undesirable noise amplification. In comparison to the conventional navigator-based segmented DWI, the new method has higher imaging throughput and better tolerance to phase variations due to local and nonlinear motions. As such, it should find broad applications in modern neuroscience investigations of detailed brain microstructures and related functions where high spatial resolution is required.

D. REFERENCES

[1] D. Le Bihan, E. Breton, D. Lallemand, M. L. Aubin, J. Vignaud, and M. Laval-Jeantet. Separation of diffusion and perfusion in intravoxel incoherent motion MR imaging. *Radiology*, 168(2):497-505, 1988.

[2] M E Moseley, Y Cohen, J Kucharczyk, J Mintorovitch, H S Asgari, M F Wendland, J Tsuruda, and D Norman. Diffusion-weighted mr imaging of anisotropic water diffusion in cat central nervous system. *Radiology*, 176(2):439-45, August 1990.

[3] P. J. Basser, J. Mattiello, and D. LeBihan. MR diffusion tensor spectroscopy and imaging. *Biophys J*, 66(1):259-67, 1994.

[4] R Turner, D Le Bihan, and A S Chesnick. Echo-planar imaging of diffusion and perfusion. *Magn Reson Med*, 19(2):247-53, June 1991.

[5] A W Anderson and J C Gore. Analysis and correction of motion artifacts in diffusion weighted imaging. *Magn Reson Med*, 32(3):379-87, September 1994.

[6] F Farzaneh, S J Riederer, and N J. Pelc. Analysis of t2 limitations and off-resonance effects on spatial resolution and artifacts in echo-planar imaging. *Magn Reson Med*, 14(1):123-39, April 1990.

[7] P Jezzard, A S Barnett, and C Pierpaoli. Characterization of and correction for eddy current artifacts in echo planar diffusion imaging. *Magn Reson Med*, 39(5):801-12, May 1998.

[8] D K Sodickson and W J. Manning. Simultaneous acquisition of spatial harmonics (smash): fast imaging with radiofrequency coil arrays. *Magn Reson Med*, 38(4):591-603, October 1997.

[9] K P Pruessmann, M Weiger, M B Scheidegger, and P Boesiger. Sense: sensitivity encoding for fast mri. *Magn Reson Med.* 42(5):952-62, November 1999.

[10] Mark A Griswold, Peter M Jakob, Robin M Heidemann, Mathias Nittka, Vladimir Jellus, Jianmin Wang, Berthold Kiefer, and Axel Haase. Generalized autocalibrating partially parallel acquisitions (grappa). *Magn Reson Med*, 47(6):1202-10, June 2002.

[11] K Butts, A de Crespigny, J M Pauly, and M Moseley. Diffusion-weighted interleaved echo-planar imagingwith a pair of orthogonal navigator echoes. *Magn Reson Med*, 35(5):763-70, May 1996.

[12] R Bammer, R Stollberger, M Augustin, J Simbrunner, H Offenbacher, H Kooijman, S Ropele, P Kapeller, P Wach, F Ebner, and F Fazekas. Diffusion-weighted Imaging with navigated interleaved echo-planar imaging and a conventional gradient system. *Radiology*, 211(3):799-806, June 1999.

[13] D Atkinson, D A Porter, D L Hill, F Calamante, and A Connelly. Sampling and reconstruction effects due to motion in diffusion-weighted interleaved echo planar imaging. *Magn Reson Med*, 44(1):101-9, July 2000.

[14] James G Pipe, Victoria G Farthing, and Kirsten P Forbes. Multishot diffusion-weighted fse using propeller mri. *Magn Reson Med*, 47(1):42-52, January 2002.

[15] Chunlei Liu, Roland Bammer, Dong•Hyum Kim, and Michael E Moseley. Self-navigated interleaved spiral (snails): application to high-resolution diffusion tensor imaging. *Magn Reson Med*, 52(6):1388-96, December 2004.

[16] Ha-Kyu Jeong, John C Gore, and Adam W Anderson. High-resolution human diffusion tensor imaging using 2-d navigated multishot sense epi at 7 t. *Magn Reson Med, May* 2012.

[17] M D Robson, A W Anderson, and J C Gore. Diffusion-weighted multiple shot echo planar imaging of humans without navigation. *Magn Reson Med*, 38(1):82-8, July 1997.

[18] Trong-Kha Truong, Nan-Kuei Chen, and Allen W Song. Inherent correction of motion-induced phase errors in multishot spiral diffusion-weighted imaging. *Magn Reson Med, December* 2011.

[19] Kala L miller and John M Pauly. Nonlinear phase correction for navigated diffusion imaging. *Magn Reson Med*, 50(2):343-53, August 2003.

[20] LI RUDIN, S OSHER and E FATEMI. Nonlinear total variation based noise removal algorithms. *Physica D*, 60(1-4):259-268, November 1992.

[21] T G Reese, 0 Heid, R M Weisskoff, and V J. Wedeen. Reduction of eddy-current-induced distortion in diffusion mri using a twice-refocused spin echo. *Magn Reson Med*, 49(1):177-82, January 2003.

[22] N.-K. Chen, A V Avram, and A W Song. Two-dimensional phase cycled reconstruction for inherent correction of echo-planar imaging nyquist artifacts. *Magn Reson Med*, 66(4):1057-66, October 2011.

[23] Christophe Lenglet, Aviva Abosch, Essa Yacoub, Federico De martino, Guillermo Sapiro, and Noam Harel. Comprehensive in vivo mapping of the human basal ganglia and thalamic connectome in individuals using 7t mri. *PloS One*, 7(1):e29153, 2012.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method of generating DWI and DTI MRI images using an MRI system, comprising:
    measuring shot-to-shot, motion-induced two dimensional (2D) phase variations of a subject inherently from acquired multiple shot echo planar imaging segments of diffusion weighted image (DWI) data without relying on any navigator signal; and
    combining parallel image reconstruction and phase-corrected EPI image reconstruction using the measured phase variations to thereby provide images corrected for motion-induced aliasing artifacts.

2. A method of generating DWI and DTI MRI images using an MRI system, comprising:
    measuring shot-to-shot, motion-induced phase variations of a subject inherently from acquired multiple shot echo planar imaging segments of diffusion weighted image (DWI) data without relying on any navigator signal to identify inter-segment phase variation from the EPI segments associated with the motion-induced 2D phase variations; and
    combining parallel image reconstruction and phase-corrected EPI image reconstruction using the measured phase variations to thereby provide images corrected for motion-induced aliasing artifacts,
    wherein the method comprises before the measuring and reconstructing steps:
    correcting acquired T2-weighted images and DWI images for Nyquist artifacts; and
    estimating coil sensitivity profiles from segmented EPI based T2-weighted images.

3. The method of claim 2, wherein the measuring comprises:
    calculating motion-induced phase variations in each of the EPI segments, wherein a respective one EPI segment is defined as a zero phase reference for the other EPI segments;
    generating phase maps based on the calculated phase variations; and
    spatially smoothing the phase maps.

4. The method of claim 3, wherein the reconstructing images is configured to generate aliasing-free DWI and/or DTI images using corrected DWI and/or DTI image data calculated using the smoothed phase maps and the estimated coil sensitivity profiles.

5. A method of generating DWI and DTI MRI images using an MRI system, comprising:
    measuring shot-to-shot, motion-induced phase variations of a subject inherently from acquired multiple shot echo planar imaging segments of diffusion weighted image (DWI) data without relying on any navigator signal; and
    combining parallel image reconstruction and phase-corrected EPI image reconstruction using the measured phase variations to thereby provide images corrected for motion-induced aliasing artifacts,
    wherein the measuring and reconstructing steps are carried out by mathematically combining parallel image reconstruction with phase-corrected EPI reconstruction using a mathematical matrix assuming magnitude signals remain unchanged across segments.

6. The method of claim 4, further comprising calculating corrected image data fractional anisotropy (FA) values using the corrected DWI and/or DTI image data.

7. A method of generating images using diffusion weighted imaging (DWI) data and/or diffusion tensor imaging (DTI) data using an MRI system that does not require navigator or reference echoes, comprising:
    electronically calculating motion-induced two dimensional (2D) phase variations across echo planar imaging (EPI) segments, wherein a respective one EPI segment is defined as a zero phase reference for at least one other EPI segment;
    applying parallel imaging reconstruction for each EPI segment using coil sensitivity data;
    applying phase-corrected segmented EPI reconstruction with the parallel imaging reconstruction; and
    generating neurological images based on the parallel imaging and segmented EPI reconstructions.

8. A method of generating images using diffusion weighted imaging (DWI) data and/or diffusion tensor imaging (DTI) data using an MRI system that does not require navigator or reference echoes, comprising:

electronically calculating motion-induced phase variations across echo planar imaging (EPI) segments, wherein a respective one EPI segment is defined as a zero phase reference for at least one other EPI segment;

applying parallel imaging reconstruction for each EPI segment using coil sensitivity data;

applying phase-corrected segmented EPI reconstruction with the parallel imaging reconstruction; and generating neurological images based on the parallel imaging and segmented EPI reconstructions, wherein the calculating phase variations is carried out based on a defined mathematical analysis that assumes that magnitude remains unchanged across multiple EPI segments, wherein the method further comprises generating phase error maps based on the calculated estimates of phase variations, and wherein the phase-corrected segmented EPI reconstruction is carried out using the phase error maps.

9. A method of generating images using diffusion weighted imaging (DWI) data and/or diffusion tensor imaging (DTI) data using an MRI system that does not require navigator or reference echoes, comprising:

electronically calculating motion-induced phase variations across echo planar imaging (EPI) segments, wherein a respective one EPI segment is defined as a zero phase reference for at least one other EPI segment;

applying parallel imaging reconstruction for each EPI segment using coil sensitivity data;

applying phase-corrected segmented EPI reconstruction with the parallel imaging reconstruction; and generating neurological images based on the parallel imaging and segmented EPI reconstructions, wherein the method comprises, before the calculating and applying reconstruction steps:

correcting acquired T2-weighted images and DWI images for Nyquist artifacts; and estimating coil sensitivity profiles from segmented EPI based T2-weighted images.

10. A method of generating images using diffusion weighted imaging (DWI) data and/or diffusion tensor imaging (DTI) data using an MRI system that does not require navigator or reference echoes, comprising:

electronically calculating motion-induced phase variations across echo planar imaging (EPI) segments, wherein a respective one EPI segment is defined as a zero phase reference for at least one other EPI segment;

applying parallel imaging reconstruction for each EPI segment using coil sensitivity data;

applying phase-corrected segmented EPI reconstruction with the parallel imaging reconstruction; and generating neurological images based on the parallel imaging and segmented EPI reconstructions, wherein the method comprises before the applying reconstruction steps, generating phase maps based on the calculated phase variations and spatially smoothing the phase maps.

11. The method of claim 10, wherein the step of generating neurological images is configured to generate aliasing-free DWI and/or DTI images with corrected DWI and/or DTI image data calculated using the smoothed phase maps and the estimated coil sensitivity profiles.

12. The method of claim 7, wherein the applying steps are carried out by mathematically combining the parallel image reconstruction with the phase-corrected EPI reconstruction using a mathematical matrix assuming magnitude signals remain unchanged across segments.

13. The method of claim 11, further comprising calculating corrected image data fractional anisotropy (FA) values using the corrected DWI and/or DTI image data.

14. A method of generating DWI and/or DTI MRI images using an MRI system, comprising:

measuring shot-to-shot, motion-induced two dimensional (2D) phase variations of a subject from acquired multiple shot echo planar imaging (EPI) segments of diffusion weighted image (DWI) data without relying on any navigator signal to identify inter-segment phase variation from the EPI segments associated with the motion-induced 2D phase variations, wherein a respective one EPI segment is defined as a zero phase reference for at least one other EPI segment; and combining parallel image reconstruction and phase-corrected EPI image reconstruction using the measured phase variations to thereby provide images corrected for motion-induced aliasing artifacts.

* * * * *